(12) United States Patent
Al-Ali et al.

(10) Patent No.: US 8,028,701 B2
(45) Date of Patent: Oct. 4, 2011

(54) RESPIRATORY MONITORING

(75) Inventors: Ammar Al-Ali, Tustin, CA (US); Mohamed K. Diab, Ladera Ranch, CA (US)

(73) Assignee: MASIMO Corporation, Irvine, CA (US)

( * ) Notice: Subject to any disclaimer, the term of this patent is extended or adjusted under 35 U.S.C. 154(b) by 1061 days.

(21) Appl. No.: 11/756,501

(22) Filed: May 31, 2007

(65) Prior Publication Data

US 2007/0277823 A1    Dec. 6, 2007

Related U.S. Application Data

(60) Provisional application No. 60/809,882, filed on May 31, 2006.

(51) Int. Cl.
*A61M 11/00* (2006.01)
(52) U.S. Cl. .......... 128/207.18; 128/204.22; 128/204.23
(58) Field of Classification Search ............ 128/206.11, 128/207.18, 204.12, 206.18, 207.13, 207.29, 128/204.22, 204.23
See application file for complete search history.

(56) References Cited

U.S. PATENT DOCUMENTS

| | | | |
|---|---|---|---|
| 4,924,876 A * | 5/1990 | Cameron ...................... 600/538 |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| 5,404,885 A * | 4/1995 | Sheehan et al. ............... 600/529 |
| D359,546 S | 6/1995 | Savage et al. |
| 5,431,170 A | 7/1995 | Mathews |
| D361,840 S | 8/1995 | Savage et al. |

(Continued)

FOREIGN PATENT DOCUMENTS

EP    1 391 178 A1    2/2004

(Continued)

OTHER PUBLICATIONS

Nanoelectronic Carbon Dioxide Detection Device Respiratory Monitoring by Nanomix, Inc. (Mar. 2005).

(Continued)

*Primary Examiner* — Steven Douglas
(74) *Attorney, Agent, or Firm* — Knobbe Martens Olson & Bear LLP

(57) ABSTRACT

A patient interface in accordance with one embodiment of the present invention is configured to be at least partially carried by a patient and to receive gas exhaled by the patient. The patient interface includes first and second cannula tubes each having a first end and a second end, the first ends are configured to be inserted into the nostrils of a patient, the first and second cannula tubes are configured to direct exhaled gas from the patient from the first ends to said second ends. The patient interface also includes first and second sensors positioned near the second ends, and the first and second sensors are configured to provide first and second signals based upon the gas, wherein the first and second signals are indicative of a physiological parameter of the patient. The patient interface also includes a communications link configured to provide the signal to a physiological monitor.

27 Claims, 4 Drawing Sheets

U.S. PATENT DOCUMENTS

| | | |
|---|---|---|
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,704,367 A | 1/1998 | Ishikawa et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,258,040 B1 | 7/2001 | Yamamori et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,422,240 B1 | 7/2002 | Levitsky et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |

| | | | |
|---|---|---|---|
| 7,132,641 B2 | 11/2006 | Schulz et al. | |
| 7,142,901 B2 | 11/2006 | Kiani et al. | |
| 7,149,561 B2 | 12/2006 | Diab | |
| 7,186,966 B2 | 3/2007 | Al-Ali | |
| 7,190,261 B2 | 3/2007 | Al-Ali | |
| 7,215,984 B2 | 5/2007 | Diab | |
| 7,215,986 B2 | 5/2007 | Diab | |
| 7,221,971 B2 | 5/2007 | Diab | |
| 7,225,006 B2 | 5/2007 | Al-Ali et al. | |
| 7,225,007 B2 | 5/2007 | Al-Ali | |
| RE39,672 E | 6/2007 | Shehada et al. | |
| 7,239,905 B2 | 7/2007 | Kiani-Azarbayjany et al. | |
| 7,245,953 B1 | 7/2007 | Parker | |
| 7,254,431 B2 | 8/2007 | Al-Ali | |
| 7,254,433 B2 | 8/2007 | Diab et al. | |
| 7,254,434 B2 | 8/2007 | Schulz et al. | |
| 7,255,107 B1 * | 8/2007 | Gomez | 128/207.13 |
| 7,272,425 B2 | 9/2007 | Al-Ali | |
| 7,274,955 B2 | 9/2007 | Kiani et al. | |
| D554,263 S | 10/2007 | Al-Ali | |
| 7,280,858 B2 | 10/2007 | Al-Ali et al. | |
| 7,289,835 B2 | 10/2007 | Mansfield et al. | |
| 7,292,883 B2 | 11/2007 | De Felice et al. | |
| 7,295,866 B2 | 11/2007 | Al-Ali | |
| 2002/0017300 A1 * | 2/2002 | Hickle et al. | 128/204.22 |
| 2003/0154981 A1 * | 8/2003 | Spruiell | 128/205.22 |
| 2004/0207529 A1 | 10/2004 | VanRyzin et al. | |
| 2005/0005942 A1 * | 1/2005 | Aylsworth et al. | 128/207.18 |
| 2005/0245836 A1 * | 11/2005 | Star et al. | 600/532 |
| 2005/0288571 A1 * | 12/2005 | Perkins et al. | 600/407 |

FOREIGN PATENT DOCUMENTS

| | | |
|---|---|---|
| EP | 1 787 670 A2 | 5/2007 |
| JP | 11 267223 | 10/1999 |
| WO | WO 01/95971 A2 | 12/2001 |
| WO | WO 03/073935 A2 | 9/2003 |
| WO | WO 2004/012577 A2 | 2/2004 |
| WO | WO 2005/069974 A2 | 8/2005 |
| WO | WO 2005/117700 A1 | 12/2005 |
| WO | WO 2006/015230 A2 | 2/2006 |

OTHER PUBLICATIONS

U.S. Appl. No. 10/940,324, Jun. 16, 2005, Gabriel, et al.
International Search Report, Nov. 23, 2007.
Written Opinion of International Searching Authority for PCT/US2007/070152, Nov. 23, 2007.

* cited by examiner

RESPIRATORY MONITORING

CROSS-REFERENCE TO RELATED APPLICATIONS

This application claims priority from U.S. Provisional No. 60/809,882, filed May 31, 2006, which is incorporated by reference herein.

BACKGROUND

1. Field of the Invention

The invention relates generally to systems, devices, and methods for monitoring a patient's respiratory system and health, including capnographers and other devices that deliver oxygen to a patient.

2. Description of the Related Art

Capnographers have been widely used for measuring concentration of carbon dioxide in a patient's exhaled breath and monitoring respiratory rate. The amount of carbon dioxide in a person's breath can indicate the overall efficiency of the cardio-pulmonary system and quality of breathing. For example, the concentration of carbon dioxide can indicate shallow breathing and poor oxygen intake. Thus, capnographers are used in hospitals and other medical institutions for monitoring the condition of a patient's respiratory system, pulmonary perfusion, and metabolism, and are most often used for patients in intensive care and under anesthesia.

A capnographer generally includes cannula tubes that conduct a patient's exhaled breath from the nasal and/or oral cavity to a collection tube that further transfers the exhaled breath to sensors. The sensors measure the concentration of carbon dioxide in the breath, and are generally located some distance away from the cannula tubes.

Capnographers are typically expensive, relatively large, and consume a large amount of power. Thus, their use is generally limited to hospitals and other controlled environments. Accordingly, there is a need for compact, inexpensive respiratory monitoring devices than can be used in and outside of hospitals to provide valuable respiratory information to doctors, nurses, paramedics, and other health care providers.

SUMMARY

A patient interface in accordance with one embodiment of the present invention is configured to be at least partially carried by a patient and to receive gas exhaled by the patient. The patient interface includes first and second cannula tubes each having a first end and a second end, the first ends are configured to be inserted into the nostrils of a patient, the first and second cannula tubes are configured to direct exhaled gas from the patient from the first ends to said second ends. The patient interface also includes first and second sensors positioned near the second ends, and the first and second sensors are configured to provide first and second signals based upon the gas and/or the contents of the gas, wherein the first and second signals are indicative of a physiological parameter of the patient. The patient interface also includes a communications link configured to provide the signal to a physiological monitor.

The patient interface can also include an information element coupled to the communications link. The information element can include calibration information regarding the first and second sensors. The patient interface can also include a filter, wherein the filter removes moisture from the gas. The first and second sensors can include nano-electric sensors or nanotechnology sensors. The first and second signals can be indicative of a carbon dioxide concentration of said gas or a respiratory rate of said patient.

In some embodiments, the communications link includes a wireless link, such as an IEEE 802.11 standard-compatible link. The patient interface can also include the physiological monitor. The physiological monitor can be configured to determine the physiological parameter from the first and second signals. In other embodiments, the length of the first and second cannula tubes is selected from the group consisting of about 1 inch, about 2 inches, about 4 inches, about six inches, and no longer than about 5 inches.

In other embodiments, the patient interface also includes a third sensor and a third cannula tube, said third cannula tube configured to be inserted into the patient's mouth and to direct breath exhaled from said patient to said third sensor. In some embodiments, the patient interface also includes a preprocessor configured to condition the first and second signals. For example, in some embodiments, the preprocessor includes a filter, an amplifier, and/or an analog-to-digital converter. In one embodiment, the patient interface is configured to be suspended from the neck of the patient.

In accordance with yet another embodiment of the present invention, a method of determining a physiological parameter of a patient, comprises: receiving gas exhaled from a patient in a patient interface carried by the patient; generating a signal indicative of a physiological parameter of said patient by sensing a parameter of said gas with a sensor positioned within said patient interface; and providing said signal to a physiological monitor.

In some embodiments, the generating a signal comprises generating a signal indicative of a carbon dioxide concentration of said gas and/or generating a signal indicative of a respiratory rate of said patient. The providing said signal can include wirelessly transmitting the signal. In other embodiments, the method also includes controlling the transfer of said gas to a selected one of two or more sensors located within said patient interface. In one embodiment, controlling the transfer of said gas extends the useful life of said patient interface.

DETAILED DESCRIPTION

Figure 1:
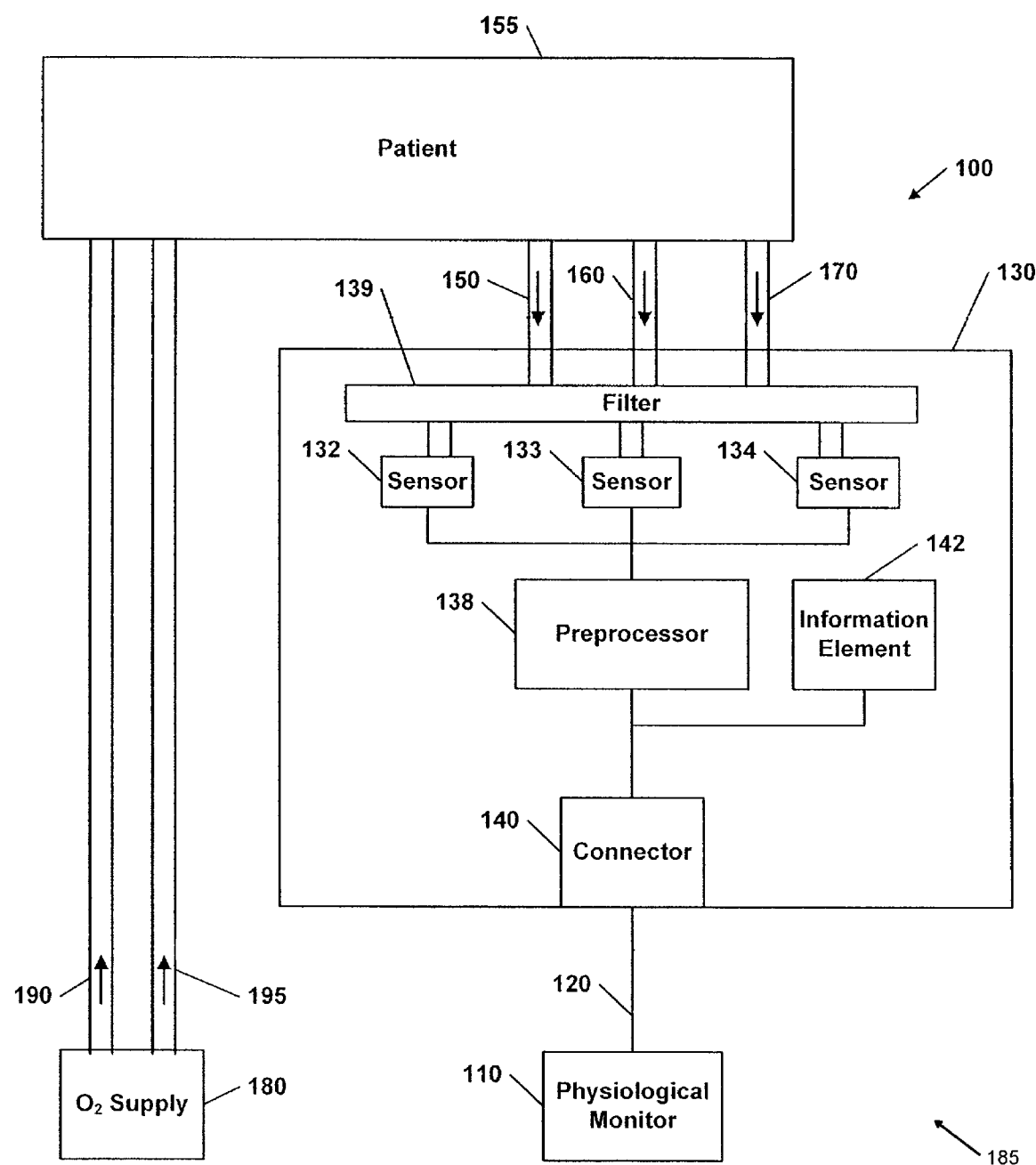
FIG. 1 is a block diagram of a respiratory monitoring system in accordance with one embodiment of the present invention.

FIG. 1 illustrates a respiratory monitoring system 100 in accordance with one embodiment of the present invention. The respiratory monitoring system 100 generally includes a physiological monitor 110 coupled to or in communication with a patient interface 185 via a communication link 120. The patient interface 185 is coupled to a patient 155. Exhaled breath from the patient 155 is received by the patient interface 185. Oxygen from an oxygen supply 180 can also be provided to the patient 155 with the patient interface 185.

The patient interface 185 of the respiratory monitoring system 100 generally includes two nasal cannulae 150, 160, e.g., tubes, for insertion into or placement adjacent the nostrils of the patient 155. The patient interface 185 may also optionally include an oral cannula tube 170 for insertion into or placement adjacent the patient's mouth. The tubes 150, 160, and 170 are configured to transfer or guide gases exhaled from the patient 155 to a carbon diode sensing module 130 of the patient interface 185. In some embodiments, the tubes are about 1 inch, about 2 inches, about 4 inches, or about six inches long. In other embodiments, the tubes are no longer than about 5 inches. In some embodiments, the patient interface 185 is configured to be carried around or suspended from the neck of the patient 155.

The system 100 may also optionally include an oxygen supply 180 for storing oxygen and providing oxygen to the patient 155. Oxygen tubes 190 and 195 facilitate the transfer of oxygen stored in the supply 180 to the patient 155. Although two tubes 190, 195 are illustrated, a single or multiple tubes may be employed. The tubes 190 and 195 may have one or more oxygen-emitting apertures (not shown) that include openings located on sections of the tubes 190 and 195 that are adjacent to the nostrils and/or the mouth of the patient.

The sensing module 130 is configured to measure a physiological parameter of the patient 155. For example, in one embodiment, the sensing module 130 measures the carbon dioxide concentration of gases exhaled by the patient 155. The sensing module 130 is further configured to generate at least one parameter signal indicative of the physiological parameter, and to transmit the parameter signal through a communications link 120 to a physiological monitor 110. The parameter signal can include measurement data, an alarm value, or any other parameter signal known to those of skill in the art.

The communications link 120 can be a wired or wireless link or a combination of a wired and a wireless link. For example, the communications link can include a single, dual, or a multi-conductor cable. A wireless communication link 120 may be established by utilizing a wireless transmitter, receiver, and/or a transceiver, such as a BLUETOOTH-compatible transceiver. In addition, a transceiver that utilizes any other wireless communication protocol, such as any of the IEEE 802.11 standards (including, but not limited to 802.11 (a), (b) or (g)), may be used.

The sensing module 130 also includes one or more sensors (e.g., sensors including or constructed using nanotechnology) located at or near the output end of the cannulae 150, 160, 170. In one embodiment, three sensors 132-134 are used. The sensors 132-134 are positioned inside of the sensing module 130 near the output ends of the cannulae 150, 160, 170. In one embodiment, the sensors are carbon dioxide sensors 132-134. The sensors 132-134 can be nanotechnology carbon dioxide sensors, or can be any of a variety of nano-sensors known to those of skill in the art. For example, the sensors 132-134 can be any sensor that monitors or measures carbon dioxide concentrations, including nanoelectric sensors described in U.S. patent application Ser. No. 10/940,324, the entirety of which is hereby incorporated by reference. Other sensors, such as infrared sensors, can also be used.

Because the sensors 132-134 are placed close to the output ends of the cannula tubes, the force of the patient's exhalation pushes the breath to be sampled into the sensors 132-134 of the sensing module 130. Unlike other systems where a pump is used to draw the patient's exhaled breath into a sensor, in some embodiments, a pump is not utilized. A sensing module that includes sensors close to the output ends of cannula tubes provides the advantage of not having to use a pump to assist in drawing the patient's exhalation from the patient's nose (or mouth), to the sensor. Another advantage provided by providing sensors at the ends of the cannula tubes, near the patient's nose (or mouth), is that ill or weak patients, with shallow breathing, can be monitored without utilizing a pump to assist in drawing the patient's exhalation to the sensor. This helps reduce the size, cost, and noise level of the sensor, sensing module, and system.

In other embodiments, a pump or other suction or vacuum device is used to help draw air from the patient to the sensors 132-134 of the sensing module 130. A filter 139 can be provided between the output of the cannulae 150, 160, 170 and the input of the sensors 132-134 to remove contaminants, moisture, mucous, and/or particulate matter from the patient's breath prior to entry into the sensor 132-134.

In addition, the sensing module 130 can also include an information element 142, a preprocessor 138, and a connector 140. The information element 142 stores information specific to each of the sensors 132-134. For example, in one embodiment, the information element 142 includes calibration parameters for each of the sensors 132-134. The information element 142 can include an EPROM, an EEPROM, a resistor, a capacitor, a microchip, a memory, a RAM, a ROM, or any other information storage element. In addition, the information element can include a combination of one or more of any of the above.

The preprocessor 138 generally includes circuitry that process the parameter signal(s) generated by the sensor 132-134 prior to transmission to the physiological monitor 110. For example, the preprocessor 138 can include any of a variety of front-end signal conditioners, such as filters, amplifiers, buffers, memories and/or analog-to-digital (A/D) converters known to those of skill in the art. The connector 140 provides a mechanical and electrical link between the patient interface 185, communication link 120, and physiological monitor 110. When the communication link 120 is a wireless link, as described above, the connector 140 can be omitted and/or can include any of the wireless transmitters, receivers, or transceivers described above.

Figure 1A:
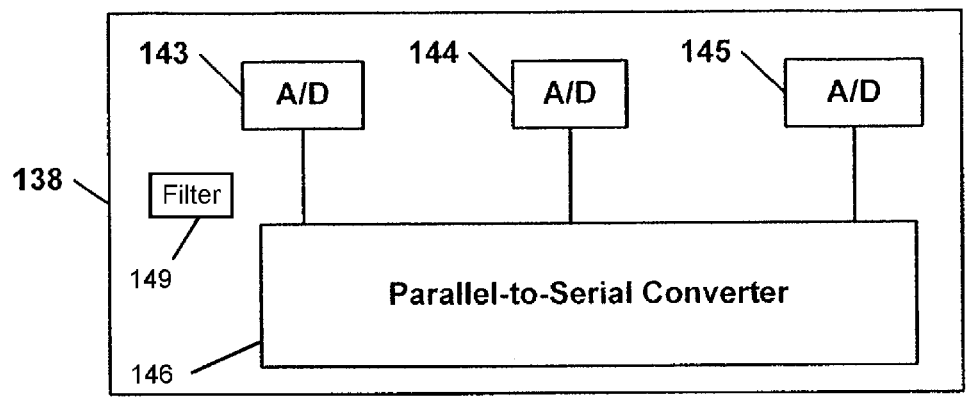
FIG. 1A is a block diagram of a preprocessing element in accordance with one embodiment of the present invention.

FIG. 1A illustrates one embodiment of the preprocessor 138. In some embodiments, the preprocessor 138 includes A/D converters 143, 144, and 145 and can further include a serial-to-parallel converter 146. Although three A/D converters 143-145 are illustrated, it should be understood that one or more A/D converters may be employed. For example, in some embodiments, a multi-channel A/D converter is provided. The A/D converters 143-145 are coupled to the sensors 132-134, respectively, and are configured to convert the analog signals outputted by the sensors 132-134 to digital signals for transmission to the physiological monitor 110. Additional front-end conditioning electronics, such as an amplifier, filter 149, and/or buffer may also be provided. The parallel converter 146 receives the digital signals from the A/D converters 143-145 and produces a serial signal that can be transmitted through a single channel communications link. The serial signal is provided to the connector 140, which passes the signal to the communications link 120, which provides the signal to the physiological monitor 110. In some embodiments, the A/D converters are provided in the physiological monitor 110, and one or more analog signals are provided from the sensing module 130 to the physiological monitor 110. In addition to the components shown, the preprocessor 138 can also include a variety of additional signal conditioning elements, such as amplifiers and/or filters. In one embodiment, the sensing module 130 may also include processing hardware such as a microprocessor, a microcontroller, a microchip, and/or memory to perform one or more of the processing functions described herein.

Figure 1B:
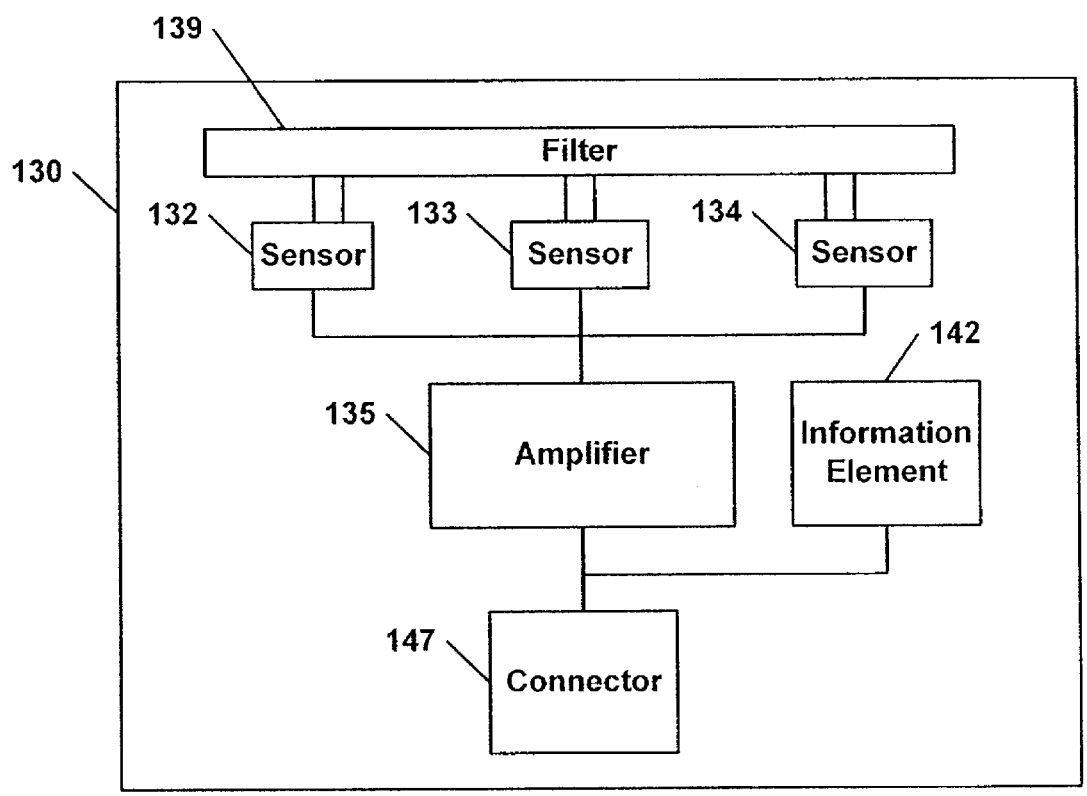
FIG. 1B is a block diagram of a sensing module in accordance with another embodiment of the present invention.

FIG. 1B illustrates another embodiment of a sensing module 130, such as a carbon dioxide sensing module, that provides analog signals to the physiological monitor 110. The sensing module 130 includes sensors 132-134 that are coupled to an amplifier 135. The amplifier 135 amplifies the signals outputted by the sensors 132-134 and provides amplified signals to the connector 147. The connector 147 provides the amplified signal to the communications link 120 to the physiological monitor 110. In this embodiment, the physiological monitor 110 converts the received analog signals to digital signals. In yet another embodiment, the sensing module 130 can include one or more A/D converters that convert the output of each of the sensors 132-134 to digital signals prior to transmission to the physiological monitor 110, as described above.

In other embodiments, one or more of the preprocessing elements are included within, and/or are performed within, the communications link 120 and/or the physiological monitor 110. For example, A/D converter, amplifier, and/or filter may be located inside the communications link 120 or the physiological monitor 110. In some embodiments, for example, preprocessing elements, such as electronics components including an A/D converter, an amplifier, and/or a filter, are included within the communications link 120. For example, the preprocessing elements can be included within the connector or the insulation of the conductors of the communications link 120.

Although in the embodiment illustrated in FIG. 1 the sensors are located inside the housing of the sensing module 130, various other configurations are also possible. For example, in one embodiment, the sensors may be placed inside each of the cannula tubes 140, 150, and 160. The output of the sensors then can be transmitted to the sensing module 130 where the signals from each of the sensors can be preprocessed and sent to the physiological monitor 110 in any of the variety of methods previously described.

In another embodiment, the cannula tubes' outputs are directed to a volume of space within the patient interface 185, such as a plenum. The plenum is generally a volume inside the sensing module 130 that is filled with the patient's exhaled gases. One or more sensors may be placed near the plenum for measuring the concentration of carbon dioxide in the gases. The signals from the sensors are then preprocessed and transmitted to the physiological monitor 110 in any of the variety of methods described above.

Some sensors, such as nanoelectric sensors, can have a limited useful life of 6-24 hours. In addition, the accuracy of such sensors may decay over time due. Thus, according to another embodiment of the present invention, the patient interface 185 can be disposable. In another embodiment, the patient interface 185 is reusable, for example, by including replaceable sensors. Thus, in such an embodiment, the sensing module 130 of the patient interface 185 is replaceable. Alternatively, the sensing module 130, itself may be disposable.

In other embodiments, to prolong the life of the sensing module 130, each cannula tube 140, 150, 160 is sequentially or serially exposed to more than one sensor over time. For example, the output of a tube is directed to a first sensor, and before the useful life of the sensor ends, the output of the tube is directed to a second sensor. In addition, for example, before the first sensor's accuracy falls bellow a predetermined level, the second sensor may be put in use. For example, before the first sensor's accuracy falls below the predetermined level, or after the passage of a predetermined amount of time, the patient interface 185 can redirect the exhaled airflow out of the cannulae to a replacement or second sensor. Any of a variety of mechanisms known to those of skill in the art can be used to redirect exhaled airflow in this manner.

For example, exchanging of the sensors may be done either manually or automatically and can be achieved in a variety of different ways. For example, the sensing module 130 can include a rotating knob that when manually turned rotates a disc or plate onto which sensors are mounted. By rotating the knob, the disc rotates with respect to the cannula output, the first sensor is moved away from the cannula output, and the second sensor is moved into position to receive exhaled air from the cannula output. In another embodiment, the cannula output and sensors are fixed in position with respect to each other, and a separation plate or disc separates the cannula output from the sensors. A window in the separation plate allows air flow from the cannula output to pass to a selected sensor. Sensors can be selected by rotating a knob. In other embodiments, the sensing module 130 includes a slideable plate that operates similarly to the rotating embodiments described above. For example, the sensors can be mounted to a slideable plate, or a slideable plate with window can be slid along its axis to control cannula to sensor coupling. Sensor selection can be performed automatically by including a motor, such as a stepper motor, linear translator, or a ratcheting mechanism, as are well known to those of skill in the art. In some cases, gear assemblies are used to control motion and orientation of the sensors with respect to the cannulae outputs.

In addition, the outputs of the cannulae can be moved or displaced with respect to the sensors. In such cases, the sensors can be mounted to the sensing module 185 and the cannulae outputs can be moved or positioned using any of the mechanisms and techniques described above.

In yet another embodiment, cannula tubes having forked outputs that can be individually opened and/or closed are provided. For example, each nostril cannula can include a first input end that is inserted into a patient's nose, and two or more output ends that are coupled to two or more sensors. For example, when the cannula has two output ends, the cannula can have a Y-shape or a T-shape. In this embodiment, one sensor can be placed at each of the forked outputs of the cannula tubes. A valve can be positioned at each of the cannula outputs that control airflow out of the cannula. In this manner, the desired sensor can be individually selected. Before the first sensor expires, the first cannula output to the first sensor is closed with a first valve and the second cannula output to the second sensor is opened with a second valve. Additional embodiments include movable cannula tubes with sensors placed at each of the possible positions of the cannula tubes or automatically exchanging the position of the sensors. Various other configurations are also possible.

One or more timers may also be provided to keep track of the length of time each of the sensors has been in operation. When any of the sensors has been in operation for a predetermined length of time, the timer may output a signal and/or trigger an alarm to notify the user that it is time to exchange the sensor. For example, the predetermined length of time can be about 2, about 4, about 5, or about 6 hours. In other cases, the predetermined time is about 5 hours, about 10 hours, about 15 hours, or about 20 hours. The output signal and/or alarm may be an audible signal such an alarm beep, a visual signal such as an LED light, a vibration, or any other known method of notifying users.

Figure 2:
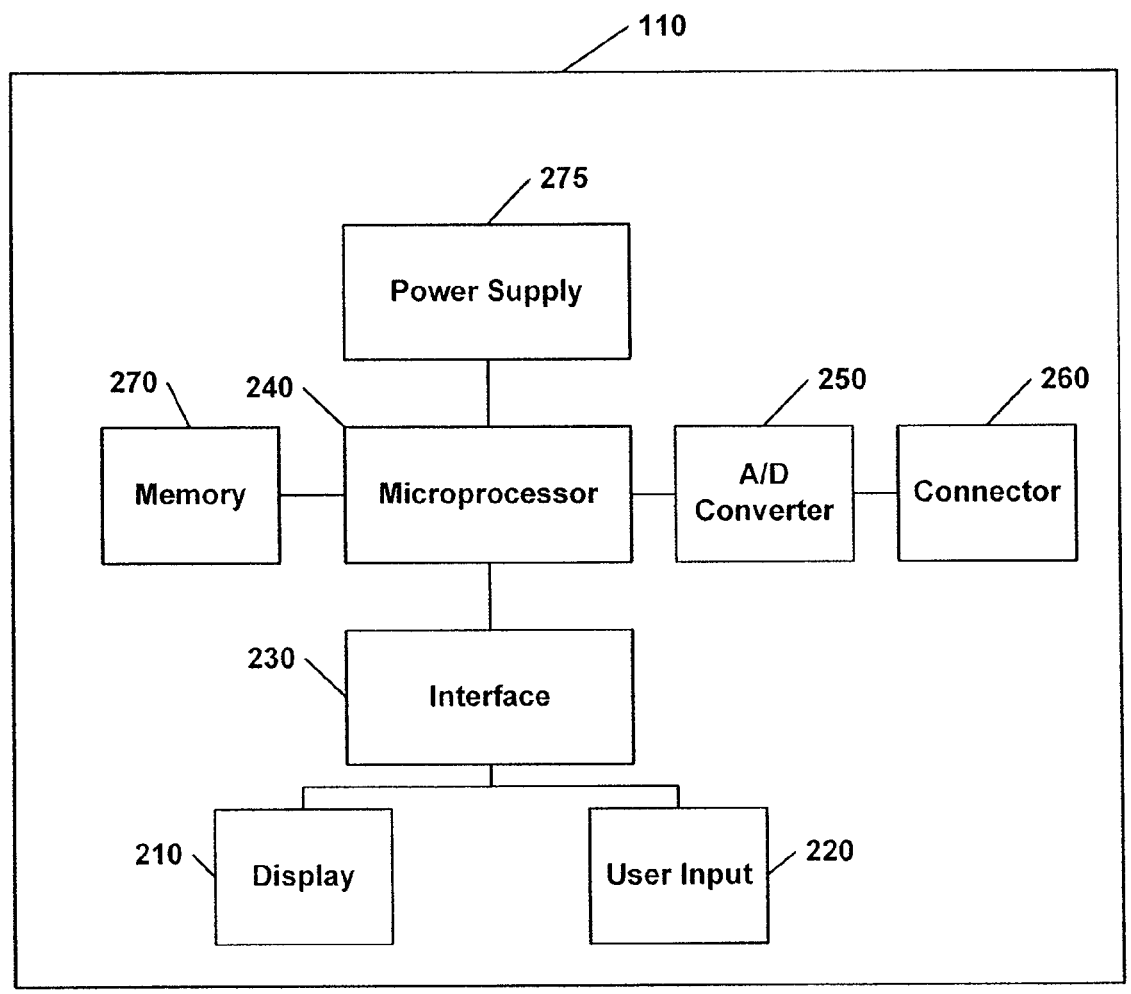
FIG. 2 is a block diagram of a physiological monitor in accordance with one embodiment of the present invention.

FIG. 2 illustrates a block diagram of a physiological monitor 110. The physiological monitor 110 can be a handheld monitor, such as a pulse oximeter, an example of which is the SpO$_2$ monitor manufactured by Masimo Corporation. The physiological monitor 110 may also be a non-handheld monitoring device, such as a computer board, or a module, such as a module that attached to a rack of monitoring equipment and/or a hospital bed. The monitor 110 generally includes a connector 260, a memory 270, a microprocessor 240, a power supply 275, an interface 230, a user input device 220, and a display 210. The connector 260 may be a transceiver and/or receiver, such as a BLUETOOTH-compatible transceiver, that is coupled to and receives signals from the patient interface 185 via the communications link 120.

Depending on whether or not the signals received by the connector 260 have already been converted to digital signals, the physiological monitor 110 may or may not include the A/D converter 250. The microprocessor analyzes the information received from the patient interface 185 and determines a physiological parameter of the patient. For example, the microprocessor can determine the CO$_2$ concentration of the patient's breath and/or the patient's respiratory rate, or breathing frequency. The physiological parameter is provided as a signal to the interface 230, which then provides the signal to the display 210. The interface 230 can include electronics, such as driver circuits, to drive the display 210 such that it displays the physiological parameter, or an indication of the physiological parameter. Indications of the physiological parameter can include an alarm, an icon, or a color that generally represents the quality of the measured physiological parameter. The memory 270 may be used to store a patient's medical data and history, for example, the history of measured physiological parameters and identification of the patient interface 185. The physiological monitor 110 can determine when it is time to replace the patient interface 185 by measuring the time the patient interface has been used. In other embodiments, the physiological monitor indicates that the patient interface 185 is to be replaced after it receives an alarm or signal from the patient interface 185. In other embodiments, the physiological monitor 110 controls the coupling of the output of the cannulae to the sensors located within the patient interface 185. As will be understood by those skilled in the art, the physiological monitor 110 may include other components as well.

Figure 3:
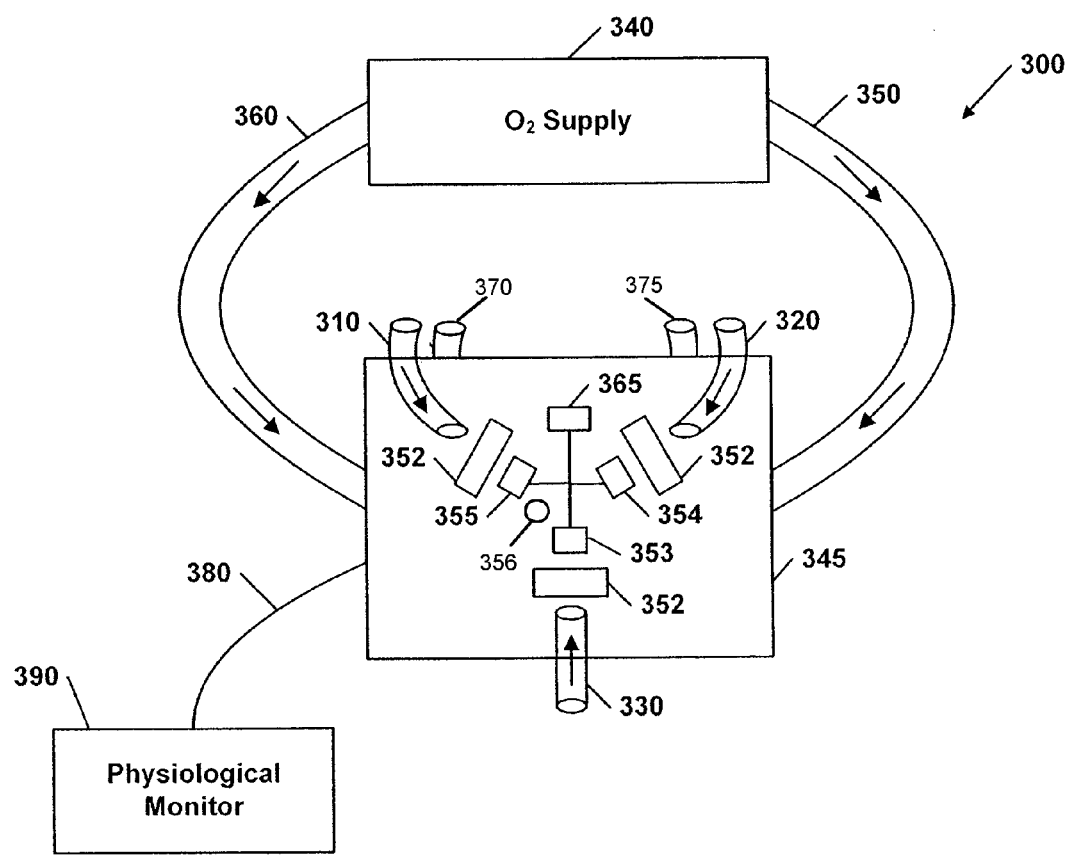
FIG. 3 is a partial front view of a respiratory monitoring system in accordance with one embodiment of the present invention.

FIG. 3 illustrates a partial front view of a respiratory monitoring system 300 in accordance with another embodiment of the present invention. The system 300 is used by inserting a first end of the cannula tubes 310, 320, and 330 into the patient's nostrils (not shown) and mouth (not shown). As the patient breathes, the gases he/she exhales enter the first end of the cannula tubes and exit from their second ends. Before entering a plenum, or volume within the sensing module 345, the gases pass through a filter 352. The filter 352 absorbs moisture, mucus, and/or other contaminants or debris contained in the gases, and protects the sensing module from contamination. After passing through the filter 352, the gases contact the sensors 353-355. The sensors 353-355 determine the concentration of a desired substance (such as carbon dioxide, alcohol, oxygen, etc.), in the exhaled gases and transfer this data to the preprocessor 365. The preprocessor 365 processes the signals and transmits them through a connector (not shown) to the physiological monitor 390 via a communications link 380, where they are further processed (as described above) and displayed to the user. The gases accumulated in the plenum then exit through an exhaust port 356 as the patient exhales the next breath. A one-way valve can be provided with the patient interface to prevent air from being drawn through the patient interface and into the patient upon patient inhalation.

As illustrated in FIG. 3, the monitoring system 300 may also include an oxygen supply 340. The oxygen supply releases oxygen into the oxygen tubes 350 and 360. Oxygen travels through the oxygen tubes and exits through oxygen emitters 370 and 375 that are located close to the nostrils and/or mouth of the patient.

In some embodiments, the monitoring system is used with patients that weigh more than about 5 kg, 10 kg, 15 kg, or 20 kg. In other embodiments, monitoring system measures carbon dioxide concentrations between about 0 and 5%, between about 0 and 10%, or between about 0 and 15%. In some embodiments, the resolution of the system is about 0.1%, about 0.0.5%, about 1% or about 1.5%. In other embodiments, the monitoring system has a response time of about 50, 100, 250, 500, or 600 μs. In other embodiments, the monitoring system has a shelf life of about one year, about 2 years, or more than one year.

Although this invention has been disclosed in the context of certain preferred embodiments, it will be understood by those skilled in the art that the present invention extends beyond the specifically disclosed embodiment to other alternative embodiments and/or uses of the invention and obvious modifications and equivalents thereof. In particular, while the present respiratory monitoring system and methods of monitoring respiration have been described in the context of a particularly preferred embodiment, the skilled artisan will appreciate, in view of the present disclosure, that certain advantages, features and aspects of the monitoring system and method may be realized in a variety of other devices. Additionally, it is contemplated that various aspects and features of the invention described can be practiced separately, combined together, or substituted for one another, and that a variety of combination and sub-combinations of the features and aspects can be made and still fall within the scope of the invention. Thus, it is intended that the scope of the present invention herein disclosed should not be limited by the particular disclosed embodiment described above, but should be determined only by a fair reading of the claims that follow.

What is claimed is:

1. A patient interface configured to be at least partially carried by a patient and to receive gas exhaled by the patient, wherein said patient interface, comprising:
    first and second cannula tubes each having a first end and a second end, said first ends configured to be inserted into the nostrils of a patient, said first and second cannula tubes configured to direct exhaled gas from the patient from said first ends to said second ends;
    first and second sensors positioned near said second ends and configured to be carried by the patient, said first and second sensors configured to provide first and second signals based upon said gas, wherein said first and second signals are indicative of a physiological parameter of said patient;
    a communications link configured to provide said signal to a physiological monitor; and
    an information element coupled to said communications link, wherein said information element comprises calibration information regarding said first and second sensors.

2. The patient interface of claim 1, further comprising a filter configured to remove moisture from said gas.

3. The patient interface of claim 1, wherein said first and second sensors comprise nano-electric sensors.

4. The patient interface of claim 1, wherein said first and second sensors comprise nanotechnology sensors.

5. The patient interface of claim 1, wherein said first and second signals are indicative of a carbon dioxide concentration of said gas.

6. The patient interface of claim 1, wherein said first and second signals are indicative of a respiratory rate of said patient.

7. The patient interface of claim 1, wherein said communications link comprises a wireless link.

8. The patient interface of claim 7, wherein said wireless link comprises an IEEE 802.11 standard compatible link.

9. The patient interface of claim 1, further comprising the physiological monitor, wherein the physiological monitor is configured to determine said physiological parameter from said first and second signals.

10. The patient interface of claim 1, wherein a length of said first and second cannula tubes is selected from the group consisting of about 1 inch, about 2 inches, about 4 inches, about six inches, and no longer than about 5 inches.

11. The patient interface of claim 1, further comprising a third sensor and a third cannula tube, said third cannula tube configured to be inserted into the patient's mouth and to direct breath exhaled from said patient to said third sensor.

12. The patient interface of claim 1, further comprising a preprocessor configured to condition said first and second signals.

13. The patient interface of claim 12, wherein said preprocessor comprises a filter.

14. The patient interface of claim 12, wherein said preprocessor comprises an amplifier.

15. The patient interface of claim 12, wherein said preprocessor comprises an analog-to-digital converter.

16. The patient interface of claim 1, wherein said patient interface is configured to be suspended from the neck of the patient.

17. A method of determining a physiological parameter of a patient, comprising:
   receiving gas exhaled from a patient in a patient interface carried by the patient, wherein said patient interface comprises at least one sensor and an information element, wherein said information element comprises calibration information regarding said at least one sensor;
   generating a signal indicative of a physiological parameter of said patient by sensing a parameter of said gas with said at least one sensor; and
   providing said signal and said calibration information to a physiological monitor.

18. The method of claim 17, wherein said generating a signal comprises generating a signal indicative of a carbon dioxide concentration of said gas.

19. The method of claim 17, wherein said generating a signal comprises generating a signal indicative of a respiratory rate of said patient.

20. The method of claim 17, wherein said providing said signal comprises wirelessly transmitting said signal.

21. The method of claim 17, wherein said at least one sensor comprises two sensors, said method further comprising controlling a transfer of said gas to a selected one of said two sensors located within said patient interface with a sensor selector, by directing said gas to said selected sensor when said sensor selector is activated.

22. The method of claim 17, wherein said at least one sensor comprises first and second sensors, said method further comprising extending a useful life of said patient interface by automatically directing said as to said second sensor when said first sensor's useful life ends.

23. The patient interface of claim 1, further comprising a third sensor and a sensor selector, wherein said sensor selector causes said exhaled gas to be directed to said third sensor when selected.

24. The patient interface of claim 23, wherein said sensor selector comprises a rotatable plate onto which said third sensor is mounted.

25. The patient interface of claim 23, wherein said sensor selector comprises a slidable plate onto which said third sensor is mounted.

26. The patient interface of claim 23, wherein said sensor selector comprises a motor.

27. The patient interface of claim 23, wherein said sensor selector is configured to control the third sensor's location with respect to one of the second ends.

* * * * *

UNITED STATES PATENT AND TRADEMARK OFFICE
CERTIFICATE OF CORRECTION

PATENT NO.        : 8,028,701 B2                                             Page 1 of 1
APPLICATION NO.   : 11/756501
DATED             : October 4, 2011
INVENTOR(S)       : Ammar Al-Ali et al.

It is certified that error appears in the above-identified patent and that said Letters Patent is hereby corrected as shown below:

In Column 5, Line 64, change "bellow" to --below--.

In Column 8, Line 44, in Claim 1, before "said" delete "wherein".

In Column 8, Line 44, in Claim 1, change "interface," to --interface--.

In Column 10, Line 23, in Claim 22, change "as" to --gas--.

In Column 10, Line 33, in Claim 25, change "slidable" to --slideable--.

Signed and Sealed this
Tenth Day of July, 2012

David J. Kappos
*Director of the United States Patent and Trademark Office*